United States Patent
Oh et al.

(10) Patent No.: US 9,126,898 B2
(45) Date of Patent: Sep. 8, 2015

(54) PROCESS FOR PREPARING PROSTAGLANDIN DERIVATIVES

(75) Inventors: Changyoung Oh, Yongin-si (KR); Kee Young Lee, Seoul (KR); Yong Hyun Kim, Suwon-si (KR); Jae Eun Joo, Suwon-si (KR)

(73) Assignee: YONSUNG FINE CHEMICAL CO., LTD., Hwaseong-Si (KR)

( * ) Notice: Subject to any disclaimer, the term of this patent is extended or adjusted under 35 U.S.C. 154(b) by 32 days.

(21) Appl. No.: 13/255,417

(22) PCT Filed: Mar. 11, 2010

(86) PCT No.: PCT/KR2010/001529
§ 371 (c)(1),
(2), (4) Date: Dec. 20, 2011

(87) PCT Pub. No.: WO2010/104344
PCT Pub. Date: Sep. 16, 2010

(65) Prior Publication Data
US 2012/0108839 A1    May 3, 2012

(51) Int. Cl.
*C07C 67/00* (2006.01)
*C07C 233/11* (2006.01)
*C07C 405/00* (2006.01)
*C07C 69/734* (2006.01)

(52) U.S. Cl.
CPC ............ *C07C 233/11* (2013.01); *C07C 69/734* (2013.01); *C07C 405/00* (2013.01); *C07C 2101/08* (2013.01)

(58) Field of Classification Search
CPC ................................................ C07C 405/0016
USPC ......................................................... 560/121
See application file for complete search history.

(56) References Cited

U.S. PATENT DOCUMENTS

| 4,785,124 | A | 11/1988 | Campbell et al. |
| 4,904,820 | A | 2/1990 | Campbell et al. |
| 4,952,710 | A | 8/1990 | Babiak et al. |
| 5,055,604 | A | 10/1991 | Babiak et al. |
| 5,075,478 | A | 12/1991 | Behling et al. |
| 5,329,035 | A | 7/1994 | Noyori et al. |
| 2001/0012907 | A1 | 8/2001 | Sato |
| 2005/0261374 | A1* | 11/2005 | Greenwood et al. ......... 514/573 |

FOREIGN PATENT DOCUMENTS

| JP | 60-9711 B2 | 3/1985 |
| JP | 06-4557 B2 | 1/1994 |
| JP | 06-49021 A | 2/1994 |
| JP | 2011-518134 A | 6/2011 |
| WO | 96/26891 A1 | 9/1996 |
| WO | 02/090324 A1 | 11/2002 |
| WO | 02/092099 A1 | 11/2002 |
| WO | 2009/141718 A2 | 11/2009 |

OTHER PUBLICATIONS

Arnett, J. Am. Chem. Soc., 1950, vol. 72, p. 5635-5638.*
Das, Chem. Rev., 2007, vol. 107, p. 3286-3337.*
Wolberg, 2006, Synthesis, No. 4, p. 557-588.*
I. V. Serkov, et al., "Prostaglandin Fluorides in Synthesis of Natural Prostaglandin Derivatives at Carboxyl Group", Russian Journal of Bioorganic Chemistry, 2009, pp. 111-117, vol. 35, No. 1.
Dan L. Eisenberg, MD, et al., "Bimatoprost and Travoprost: A Review of Recent Studies of Two New Glaucoma Drugs", Survey of Ophthalmology, Aug. 2002, pp. S105-S115, vol. 47, Supplement 1.
Abdul H. Khan, et al., "Effect of femto to nano molar concentrations of prostaglandin analogues on pregnant rat uterine contractility", European Journal of Pharmacology, 2008, pp. 185-190, vol. 581.
E. J. Corey, et al., "Stereo-Controlled Synthesis of Prostaglandins $F_{2\alpha}$ and $E_2$ (dl)" Journal of the American Chemical Society, Sep. 24, 1969, pp. 5675-5677, vol. 91, No. 20.
James R. Behling, et al., "In Situ Cuprate Formation via Transmetalation between Vinylstannanes and Higher Order Cyanocuprates", Journal of American Chemical Society, 1988, pp. 2641-2643, vol. 110, No. 8.
Japanese Patent Office, Office Action dated May 28, 2013 issued in Japanese Application No. 2011-553956.
Japanese Patent Office, Office Action Dated Nov. 26, 2013 issued in Japanese Application No. 2011-553956.
Korea Intellectual Property Office, Korean Office Action mailed Dec. 28, 2010 in corresponding Korean Patent Application No. 10-2009-0020920.

* cited by examiner

*Primary Examiner* — Rebecca Anderson
*Assistant Examiner* — Karen Cheng
(74) *Attorney, Agent, or Firm* — Sughrue Mion, PLLC

(57) ABSTRACT

The present invention relates to a process for preparing a prostaglandin derivative and an intermediate therefor. In accordance with the present invention, the prostaglandin F (PGF) derivative can be efficiently prepared with high purity by removing the protecting group of a protected prostaglandin E (PGE) derivative obtained from conjugate addition and then stereoselectively reducing the ketone group on the cyclopentanone ring of the PGE derivative.

16 Claims, No Drawings

PROCESS FOR PREPARING PROSTAGLANDIN DERIVATIVES

CROSS REFERENCE TO RELATED APPLICATION

This application is a National Stage of International Application No. PCT/KR2010/001529 filed Mar. 11, 2010, claiming priority based on Korean Patent Application No. 10-2009-0020920, filed Mar. 11, 2009, the contents of all of which are incorporated herein by reference in their entirety.

TECHNICAL FIELD

The present invention relates to a process for efficiently preparing a prostaglandin derivative with high purity and an intermediate therefor.

BACKGROUND ART

Prostaglandin derivatives, particularly travoprost, bimatoprost and latanoprost of the following formula (2) have been extensively used due to their clinical effects such as reducing intraocular pressure and promoting hair and eyelash growth.

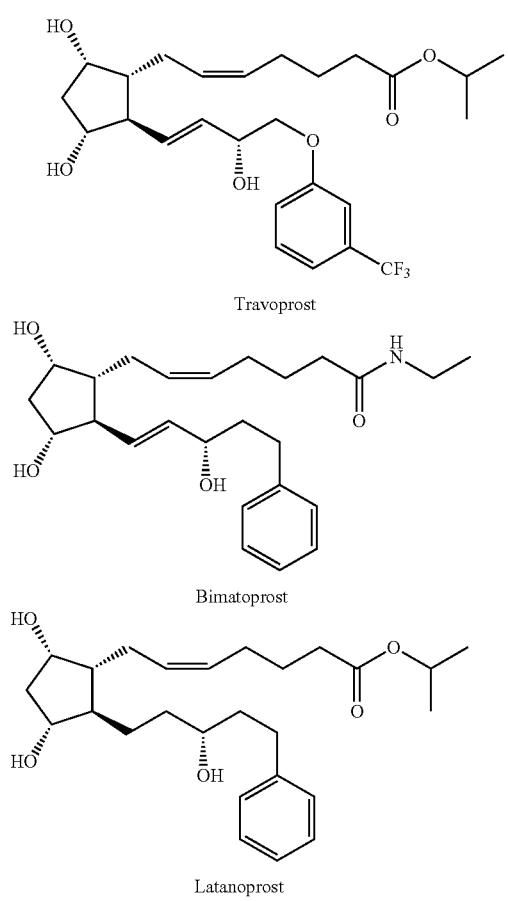

The prostaglandin derivatives have been conventionally prepared through many synthetic steps in poor yields. The most common commercial processes use Corey lactone as a starting material to produce the prostaglandin derivatives, as shown in the following Reaction Scheme 1 (see E. J. Corey et al., J. Amer. Chem. Soc., 91, 5675-5677, 1969). However, Corey lactone is expensive and the processes require a chromatographic separation for removing β-OH which is produced as a by-product on the reduction of 15-ketone group into α-OH after the introduction of ω-chain. Therefore, the processes are unsuitable for large-scale production of the prostaglandin derivatives in terms of poor yields and high costs. The β-OH produced as a by-product may be reduced by using a chiral borane compound as a stereoselective reducing agent, but the chiral borane compound is also very expensive.

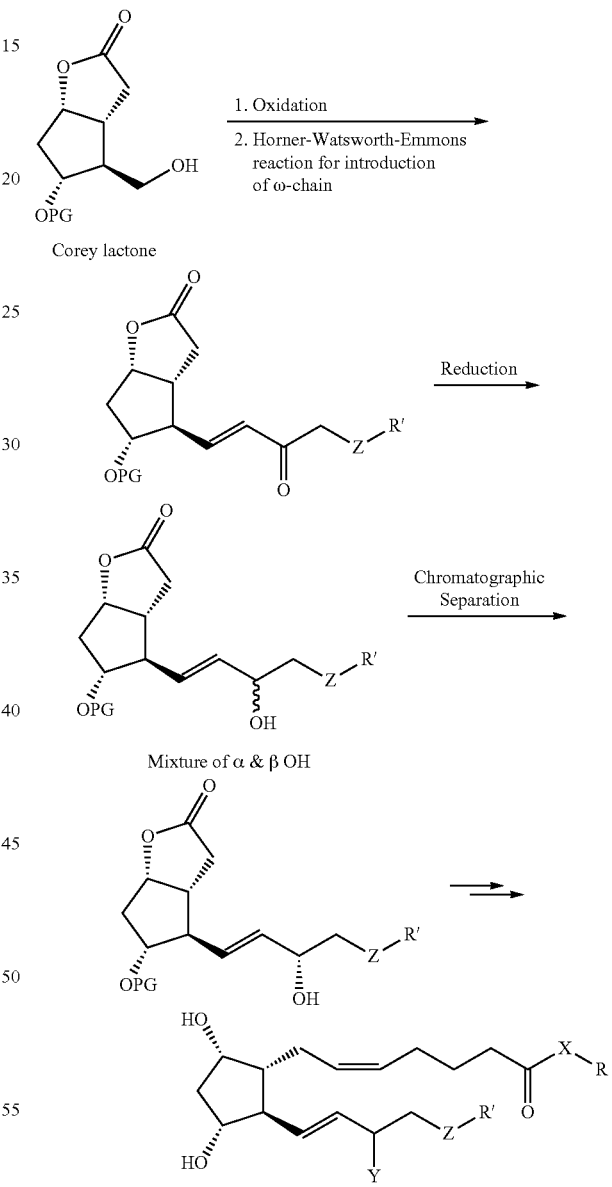

To overcome the above disadvantages, it was suggested to prepare the prostaglandin derivatives by conjugate addition of ω-chain including α-OH to cyclopentenone derivatives having α-side chain, as shown in the following Reaction Scheme 2. In particular, a process developed by Lipshuts et al. can stereoselectively introduce ω-chain by using higher order mixed organocuprate (see U.S. Pat. Nos. 4,785,124, 4,904,820, 4,952,710 and 5,055,604, and WO 02/090324).

[Reaction Scheme 2]

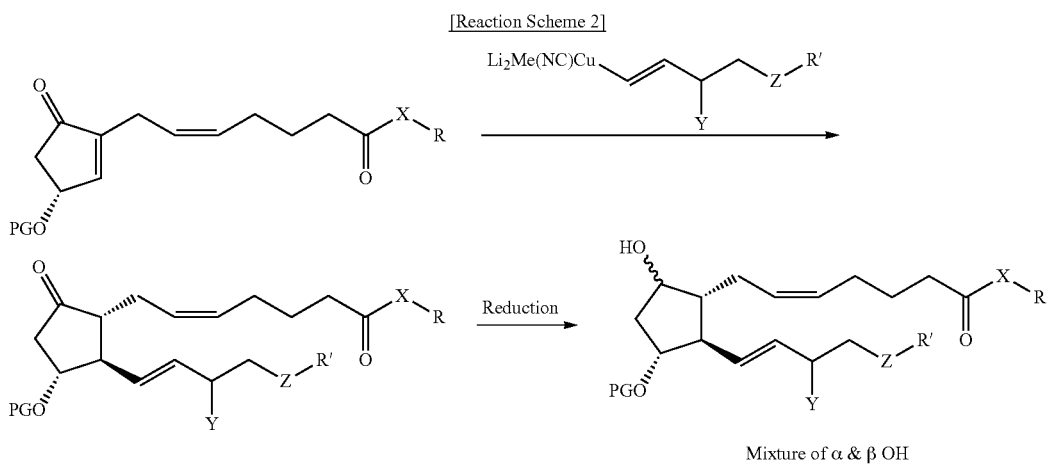

Mixture of α & β OH

Such process requires that, in order to synthesize prostaglandin F (PGF) derivatives, the ketone group on the cyclopentanone ring of the prostaglandin E (PGE) derivatives obtained from the conjugate addition should be stereoselectively reduced to α-OH. The use of sodium borohydride (NaBH$_4$) as a reducing agent gives the PGF derivatives in the form of a 6:4 mixture of α-OH and β-OH, and the use of a bulky hydride such as L-selectride, N-selectride, K-selectride and LS-selectride gives the PGF derivatives in increased selectivity of 9:1 (α:β ratio). However, a significant amount of β OH should be still removed by using a difficult method causing large yield loss.

Therefore, there has been a need to develop a process for more stereoselectively reducing the ketone group on the cyclopentanone ring of the prostaglandin E derivatives.

DISCLOSURE

Technical Problem

The present inventors have endeavored to overcome the above problems and found that a highly pure PGF derivative having little or no β-OH can be efficiently prepared by removing the protecting group of the prostaglandin E (PGE) derivative obtained from conjugate addition and then stereoselectively reducing the ketone group on the cyclopentanone ring.

An object of the present invention is, therefore, to provide a process for efficiently preparing a PGF derivative with high purity.

Another object of the present invention is to provide a novel intermediate used in said process.

Technical Solution

One aspect of the present invention relates to a process for preparing a prostaglandin F (PGF) derivative of the following formula (1), which comprises the steps of:

(i) removing the hydroxy protecting group of a protected prostaglandin E (PGE) derivative of the following formula (5) to give a prostaglandin E (PGE) derivative of the following formula (6); and (ii) stereoselectively reducing the ketone group on the cyclopentanone ring of the compound of the following formula (6):

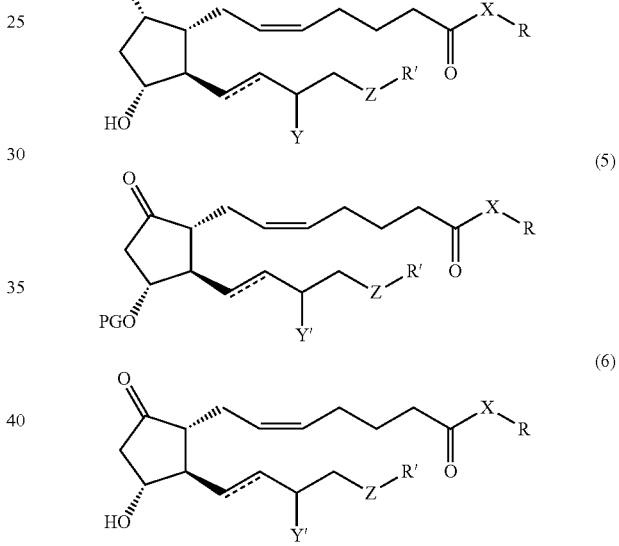

wherein,
------ is a single or double bond;
X is O or NH;
Y is α-OH or difluoro, preferably α-OH;
Y' is α—OPG or difluoro, preferably α—OPG;
Z is CH$_2$, O or S, preferably CH$_2$ or O;
R is H or C$_1$-C$_5$ alkyl, preferably C$_1$-C$_5$ alkyl;
R' is C$_1$-C$_5$ alkyl, C$_3$-C$_7$ cycloalkyl or aryl, preferably phenyl optionally substituted by C$_1$-C$_5$ haloalkyl or halogen, more preferably CF$_3$, Cl or F, most preferably CF$_3$; and
PG is a hydroxy protecting group, preferably tetrahydropyranyl, trimethylsilyl, triethylsilyl or t-butyldimethylsilyl, more preferably triethylsilyl.

The term "C$_1$-C$_5$ alkyl" as used herein means a straight or branched hydrocarbon having 1 to 5 carbon atoms, which includes methyl, ethyl, n-propyl, propyl, n-butyl, i-butyl, s-butyl, t-butyl, n-pentyl, etc., but is not limited thereto.

The term "C$_3$-C$_7$ cycloalkyl" as used herein means a cyclic hydrocarbon having 3 to 7 carbon atoms, which includes cyclopropyl, cyclobutyl, cyclopentyl, cyclohexyl, etc., but is not limited thereto.

The term "aryl" as used herein includes all of aromatic group, heteroaromatic group and partially reduced derivatives thereof. The aromatic group means a 5 to 15-membered simple or fused ring. The heteroaromatic group means an aromatic group containing at least one atom selected from oxygen, sulfur and nitrogen. Examples of the aryl include phenyl, naphthyl, pyridinyl, furanyl, thiophenyl, indolyl, quinolinyl, imidazolinyl, oxazolyl, thiazolyl, tetrahydronaphthyl, etc., but are not limited thereto.

The $C_1$-$C_5$ alkyl, $C_3$-$C_7$ cycloalkyl and aryl may have one or more hydrogens substituted by $C_1$-$C_5$ alkyl, $C_2$-$C_6$ alkenyl, $C_2$-$C_6$ alkynyl, $C_3$-$C_{10}$ cycloalkyl, $C_1$-$C_5$ haloalkyl, $C_1$-$C_5$ alkoxy, $C_1$-$C_5$ thioalkoxy, aryl, acyl, hydroxy, thio, halogen, amino, alkoxycarbonyl, carboxyl, carbamoyl, cyano, nitro, etc.

The process of the present invention is, hereinafter, described in more detail referring to the following Reaction Scheme 3.

to its cuprate, followed by conjugate addition to a cyclopentenone compound of the following formula (4), according to a known method (see J. Am. Chem. Soc. 1988, 110, 2641-2643).

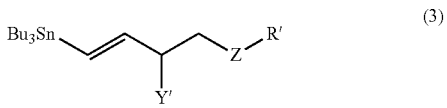

(3)

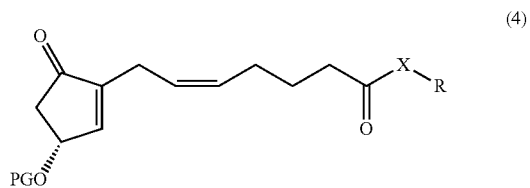

(4)

[Reaction Scheme 3]

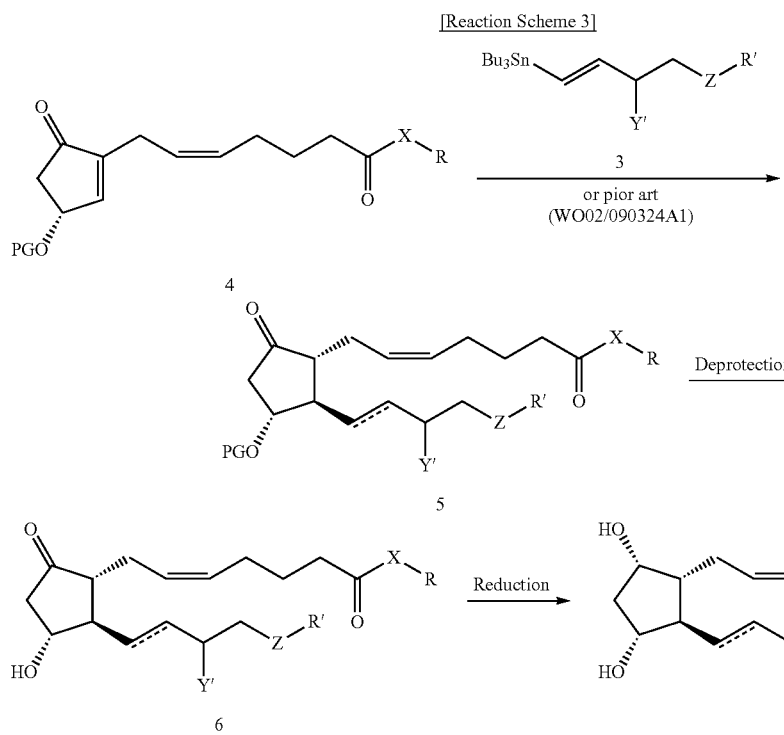

Step 1: Preparation of Prostaglandin E (PGE) Derivative of Formula (6)

The prostaglandin E (PGE) derivative of formula (6) is prepared by removing the hydroxy protecting group of the protected PGE derivative of formula (5).

The deprotection may be carried out under an acidic condition. Particularly, silyl protecting groups may be deprotected by using various fluoride compounds.

The acidic condition for silyl protecting groups may be provided by the use of d-HCl, an aqueous $NaHSO_4$ solution, pyridinium p-toluensulfonate (PPTS), etc. Preferably, PPTS is used in a catalytic amount in a mixture of acetone and water. Examples of the fluoride compounds include tetrabutylammonium fluoride ($Bu_4N^+F^-$), hydrogen fluoride-pyridine (HF-pyridine), fluorosilicic acid ($H_2SiF_6$), etc., but are not limited thereto.

The compound of formula (5) having a carbon-carbon double bond at 13 and 14 position may be prepared by converting an alkenyl tin compound of the following formula (3)

Preferably, the alkenyl tin compound of formula (3) is added to a solution of $Me_2Cu(CN)Li_2$ and converted to a higher order mixed cuprate of the following formula (7), which is subjected to conjugate addition to the cyclopentenone compound of formula (4).

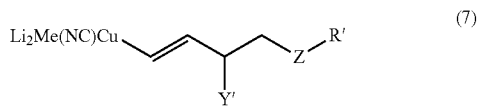

(7)

The above reaction is preferably carried out in a mixture of tetrahydrofuran (THF) and hexane or a mixture of THF and ether, most preferably a mixture of THF and diethyl ether, as a solvent.

The conjugate addition is preferably carried out in a low temperature of −60° C. or less.

The alkenyl tin compound of formula (3) may be prepared by reacting a ω-chain precursor containing a terminal acetylene group with Bu₃SnH, according to a known method (see J. Am. Chem. Soc. 1988, 110, 2641-2643).

Meanwhile, the compound of formula (5) having a carbon-carbon single bond at 13 and 14 position may be prepared by the method disclosed in WO 02/090324.

Step 2: Preparation of Prostaglandin F (PGF) Derivative of Formula (1)

The prostaglandin F (PGF) derivative of formula (1) is prepared by stereoselectively reducing the ketone group on the cyclopentanone ring of the compound of formula (6).

A reducing agent used in the present invention includes sodium borohydride (NaBH₄), L-selectride, N-selectride, K-selectride, LS-selectride, 2,6-di-tert-butyl-4-methyl phenol and diisobutyl aluminium hydride (DIBAL), etc., but is not limited thereto. Preferably, 2,6-di-tert-butyl-4-methyl phenol and DIBAL are used.

The use of 2,6-di-tert-butyl-4-methyl phenol and DIBAL leads to stereoselective preparation of α-OH compound having no β-OH. Generally, the reduction is carried out by reacting 2,6-di-tert-butyl-4-methyl phenol in an amount of 2 to 10 equivalents, preferably 5 equivalents with DIBAL in an amount of 2 to 5 equivalents, preferably 4 equivalents in toluene as a solvent at −10 to 10° C., preferably 0° C. for 1 to 2 hours, preferably 1 hour; lowering the temperature of the reaction solution to −70° C.; adding the compound of formula (6) thereto, followed by stirring for 1 to 3 hours, preferably 2 hours; raising the temperature of the reaction solution to −40 to −20° C., preferably −30° C.; and stirring the reaction solution for 3 to 6 hours, preferably 4 hours.

Alternatively, the prostaglandin F (PGF) derivative of formula (1) wherein X is NH may be prepared by reacting the PGF derivative of formula (1) wherein X is O and R is methyl, with RNH₂.

The above reaction is preferably carried out at room temperature.

Examples of the prostaglandin F (PGF) derivative of formula (1) prepared by the present process include travoprost, bimatoprost and latanoprost, which are widely used due to their clinical effects such as reducing intraocular pressure and promoting hair and eyelash growth. According to the present invention, travoprost, bimatoprost and latanoprost can be prepared with high purity of 99.5% or more by further comprising the step of purifying them by HPLC using a mixture of hydrocarbon and alcohol, preferably a mixture of n-hexane and anhydrous ethanol or a mixture of n-heptane and anhydrous ethanol, or a mixture of dichloromethane and alcohol, preferably a mixture of dichloromethane and isopropanol.

Another aspect of the present invention relates to a compound of the following formula (8), which is an intermediate of travoprost, and a compound of formula (9), which is an intermediate of bimatoprost.

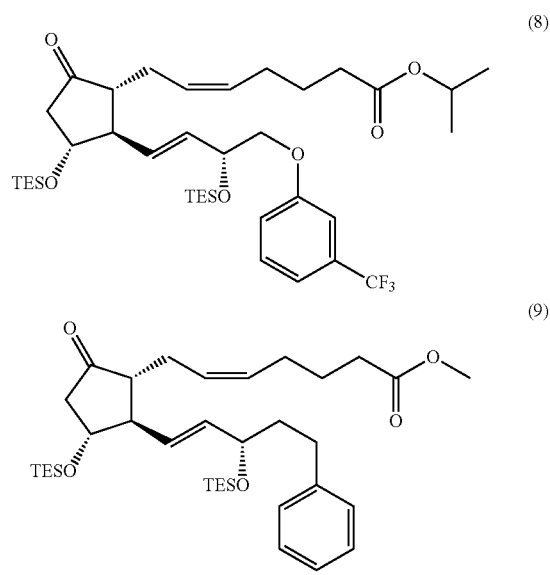

Advantageous Effects

In accordance with the present invention, the prostaglandin F (PGF) derivative can be efficiently prepared with high purity by removing the protecting group of the protected prostaglandin E (PGE) derivative obtained from conjugate addition and then stereoselectively reducing the ketone group on the cyclopentanone ring of the PGE derivative. Particularly, the α-OH compound having no β-OH can be stereoselectively prepared using 2,6-di-tert-butyl-4-methyl phenol and diisobutyl aluminium hydride (DIBAL) as a reducing agent.

BEST MODE

The present invention is further illustrated by the following examples, which are not to be construed to limit the scope of the invention.

Example 1

Preparation of Compound (8)

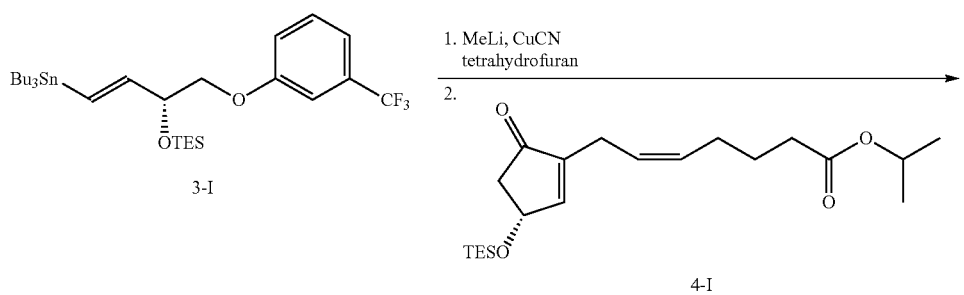

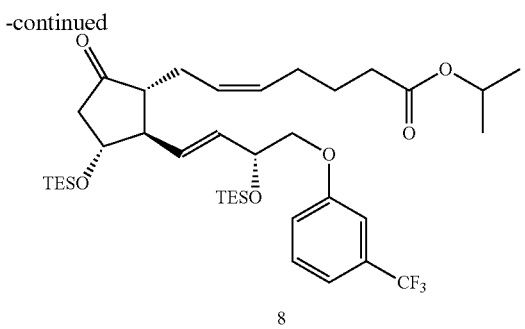

Copper cyanide (30 g) was dissolved in THF (680 ml), followed by cooling to 0° C., and methyllithium (1.6 M diethyl ether, 445 ml) was added dropwise thereto. The resulting reaction solution was stirred for 10 to 20 minutes, and compound (3-I) (215 g) dissolved in THF (200 ml) was added thereto. The resulting reaction solution was stirred for 1.5 to 2 hours, followed by cooling to −70° C., and compound (4-I) (90 g) dissolved in THF (680 ml) was rapidly added thereto, and then the temperature of the reaction solution was slowly raised to −45° C. After the reaction was completed, the resulting reaction solution was added to a mixture of aqueous ammonium chloride solution/ammonia water (9:1, 1.8 L) and diethyl ether (2 L), followed by stirring at room temperature for 1 to 2 hours. The organic layer was separated, dried over sodium sulfate (1 kg), filtered and concentrated. The resulting residue was subjected to chromatography (eluent: n-hexane:ethyl acetate=10:1) to give the target compound (127 g, Yield: 75%).

Example 2

Preparation of Compound (6-I)

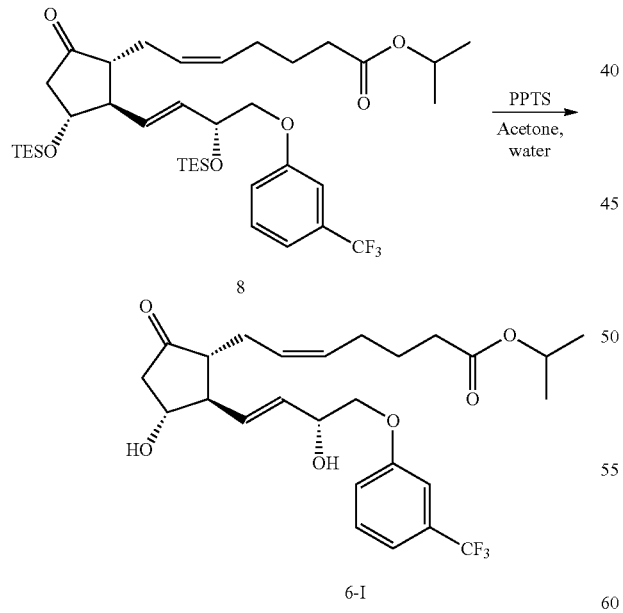

Pyridinium p-toluensulfonate (PPTS, 2.3 g) was added to compound (8) (127 g) dissolved in a mixture of acetone (1.2 L) and water (0.25 L), followed by stirring at room temperature for 12 hours. After the reaction was completed, the resulting reaction solution was concentrated under vacuum, and ethyl acetate (1.5 L) and water (1 L) were added thereto, followed by stirring. The organic layer was separated, dried over sodium sulfate (1 kg), filtered and concentrated. The resulting residue was subjected to chromatography (eluent: n-hexane:ethyl acetate=1:3) to give the target compound (78 g, Yield: 89%).

Example 3

Preparation of Travoprost

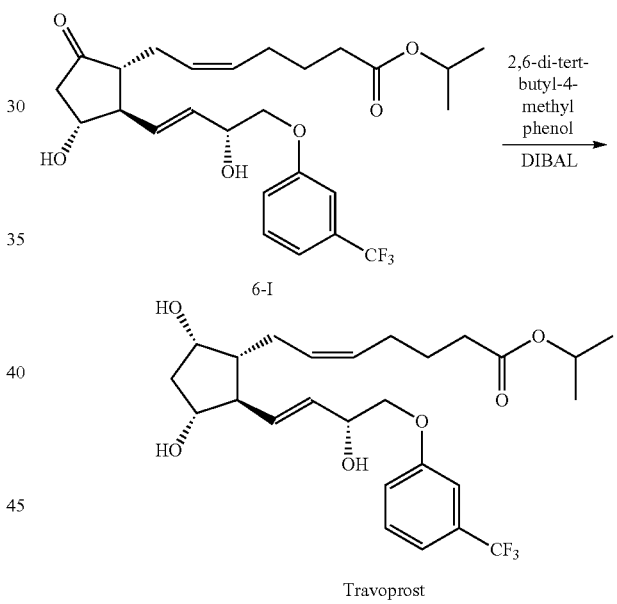

2,6-Di-tert-butyl-4-methyl phenol (172 g) was dissolved in toluene (2 L), followed by cooling to 0° C., and DIBAL (1.0 M toluene, 625 ml) was added dropwise thereto for 1 hour. The resulting reaction solution was cooled to −70° C., and compound (6-I) (78 g) dissolved in toluene (0.5 L) was added dropwise thereto. The resulting reaction solution was stirred for about 2 hours, and its temperature was slowly raised to −40 to −20° C., followed by stirring for 4 hours. After the reaction was completed, an aqueous 2N hydrochloric acid solution (1 L) was added. The organic layer was separated, dried over sodium sulfate (1 kg), filtered and concentrated. The resulting residue was subjected to chromatography (eluent: n-hexane:ethyl acetate=1:5) to give travoprost (Purity: 96% or more). The obtained compound was subjected to preparative HPLC (eluent: dichloromethane:isopropanol=90:10) to give highly pure travoprost (50 g, Purity: 99.5% or more, Yield: 63%).

Example 4

Preparation of Compound (9)

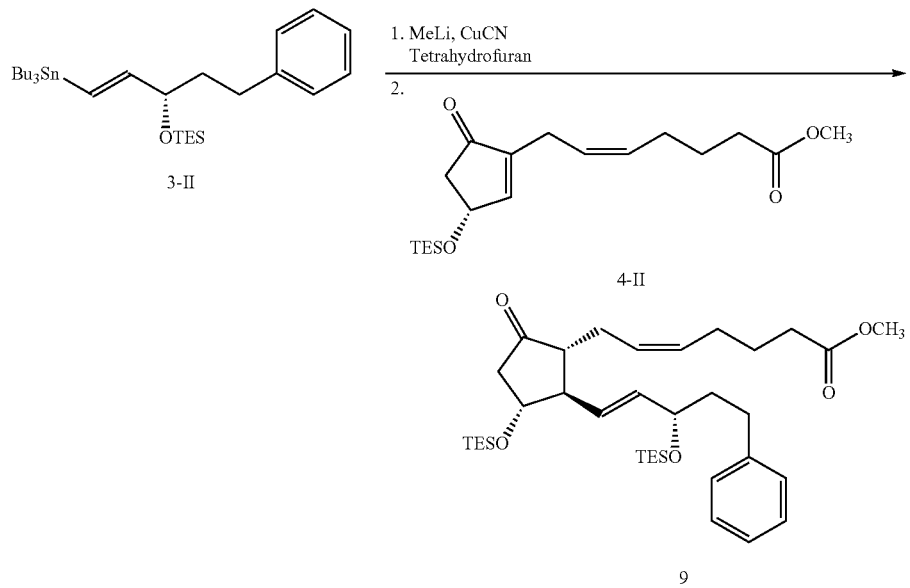

Copper cyanide (98 g) was dissolved in THF (2.2 L), followed by cooling to 0° C., and methyllithium (1.6 M diethyl ether, 1.44 L) was added dropwise thereto. The resulting reaction solution was stirred for 10 to 20 minutes, and compound (3-II) (598 g) dissolved in THF (1.4 L) was added thereto. The resulting reaction solution was stirred for 1.5 to 2 hours, followed by cooling to −70° C., and compound (4-II) (270 g) dissolved in THF (2.2 L) was added thereto for 15 minutes, and then the temperature of the reaction solution was slowly raised to −45° C. After the reaction was completed, the resulting reaction solution was added to a mixture of aqueous ammonium chloride solution/ammonia water (9:1, 7.0 L) and diethyl ether (3.5 L), followed by stirring at room temperature for 1 to 2 hours. The organic layer was separated, dried over sodium sulfate (1 kg), filtered and concentrated. The resulting residue was subjected to chromatography (eluent: n-hexane:ethyl acetate=10:1) to give the target compound (420 g, Yield: 88%).

Example 5

Preparation of Compound (6-II)

Pyridinium p-toluensulfonate (PPTS, 8.8 g) was added to compound (9) (420 g) dissolved in a mixture of acetone (4.3 L) and water (0.83 L), followed by stirring at room temperature for 12 hours. After the reaction was completed, the resulting reaction solution was concentrated under vacuum, and ethyl acetate (5.0 L) and water (2.0 L) were added thereto, followed by stirring. The organic layer was separated, dried over sodium sulfate (1 kg), filtered and concentrated. The resulting residue was subjected to chromatography (eluent: n-hexane:ethyl acetate=1:3) to give the target compound (205 g, Yield: 76%).

Example 6

Preparation of Compound (1-I)

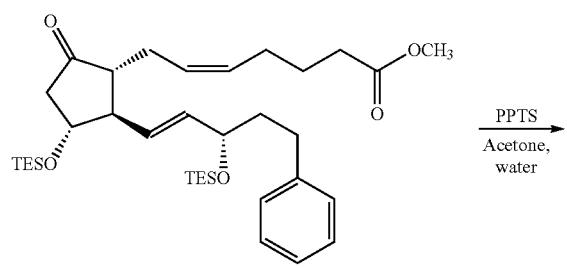

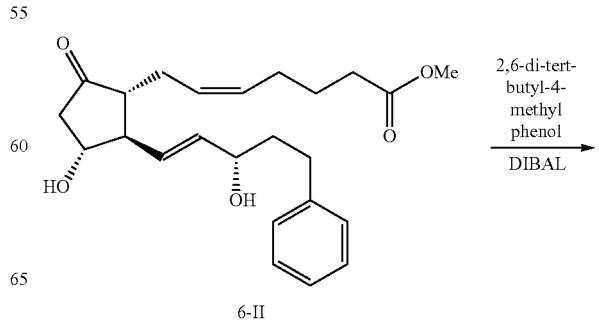

-continued

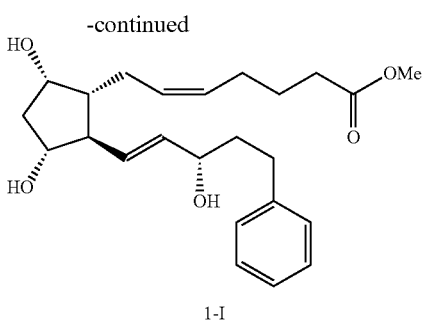

1-I 2,6-Di-tert-butyl-4-methyl phenol (560 g) was dissolved in toluene (6.5 L), followed by cooling to 0° C., and DIBAL (1.0 M toluene, 2.05 L) was added dropwise thereto for 1 hour. The resulting reaction solution was cooled to −70° C., and compound (6-II) (205 g) dissolved in toluene (1.6 L) was added dropwise thereto. The resulting reaction solution was stirred for about 2 hours, and its temperature was slowly raised to −40 to −20° C., followed by stirring for 4 hours. After the reaction was completed, an aqueous 2N hydrochloric acid solution (2.5 L) was added. The organic layer was separated, dried over sodium sulfate (1 kg), filtered and concentrated. The resulting residue was subjected to chromatography (eluent: n-hexane:ethyl acetate=1:5) to give the target compound (155 g, Yield: 76%).

Example 7

Preparation of Bimatoprost

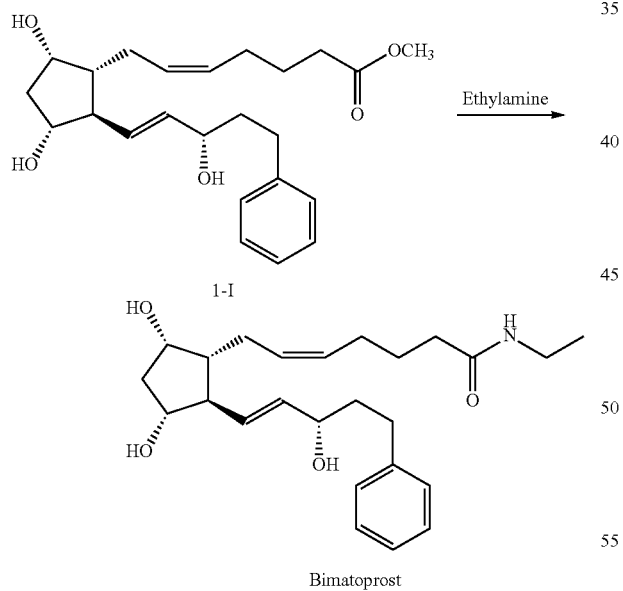

Bimatoprost

Compound (1-I) (155 g) was added to a 70% aqueous solution of ethylamine (3.0 L), followed by stirring at room temperature for 60 hours. After the reaction was completed, the resulting reaction solution was concentrated to be its half level under reduced pressure, neutralized with a 2M aqueous solution of sodium hydrogensulfate (3.0 L, pH=4-5) and extracted with ethyl acetate (3.0 L). The organic layer was dried over sodium sulfate (1 kg), filtered and concentrated. The resulting residue was subjected to preparative HPLC (eluent: n-hexane:anhydrous ethanol=90:10), concentrated, and crystallized with diethyl ether (1.5 L). The resulting solid was filtered and dried under vacuum to give highly pure bimatoprost (100 g, Purity: 99.5% or more, Yield: 62%).

Example 8

Preparation of Compound (6-III)

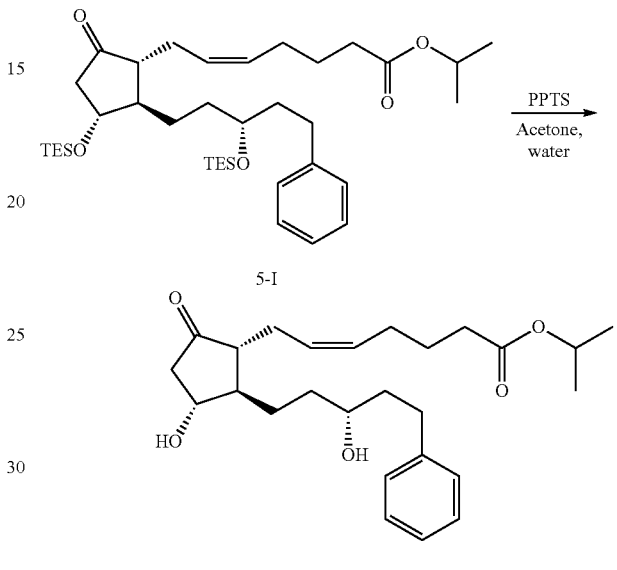

Pyridinium p-toluensulfonate (PPTS, 4.3 g) was added to compound (5-I) (217 g) dissolved in a mixture of acetone (1.2 L) and water (0.2 L), followed by stirring at room temperature for 12 hours. After the reaction was completed, the resulting reaction solution was concentrated under vacuum, and ethyl acetate (1.5 L) and water (1.0 L) were added thereto, followed by stirring. The organic layer was separated, dried over sodium sulfate (1 kg), filtered and concentrated. The resulting residue was subjected to chromatography (eluent: n-hexane:ethyl acetate=1:3) to give the target compound (128 g, Yield: 90%).

Example 9

Preparation of Latanoprost

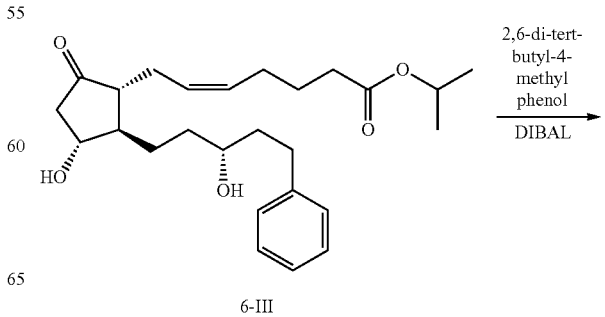

6-III

-continued

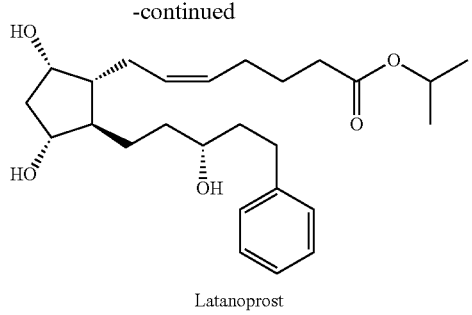

Latanoprost 2,6-Di-tert-butyl-4-methyl phenol (408 g) was dissolved in toluene (3.7 L), followed by cooling to 0° C., and DIBAL (1.0 M toluene, 1484 ml) was added dropwise thereto for 1 hour. The resulting reaction solution was stirred at the same temperature for 1 hour, cooled to −70° C., and compound (6-III) (128 g) dissolved in toluene (128 ml) was added dropwise thereto. The resulting reaction solution was stirred at the same temperature for about 2 hours, and its temperature was slowly raised to −40 to −20° C., followed by stirring for 4 hours. After the reaction was completed, an aqueous 2N hydrochloric acid solution (1.8 L) was added. The organic layer was separated, dried over sodium sulfate (1 kg), filtered and concentrated. The resulting residue was subjected to chromatography (eluent: n-hexane:ethyl acetate=1:3) to give latanoprost (Purity: 96% or more). The obtained compound was subjected to preparative HPLC (eluent: heptane:anhydrous ethanol=94:6) to give highly pure latanoprost (96 g, Purity: 99.8% or more, Yield: 75%).

The invention claimed is:

1. A process for preparing a prostaglandin F of the following formula (1), which comprises the steps of:
   (i) removing the hydroxy protecting group of a protected prostaglandin E of the following formula (5) to give a prostaglandin E of the following formula (6); and
   (ii) stereoselectively reducing the ketone group on the cyclopentanone ring of the compound of the following formula (6) to give the prostaglandin F:

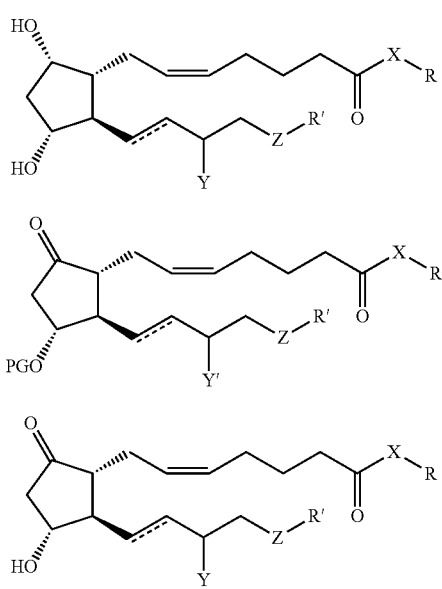

wherein,
z,25 is a single or double bond;
X is O or NH;
Y is α-OH or difluoro;
Y' is α-OPG or difluoro;
Z is $CH_2$, O or S;
R is H or $C_1$-$C_5$ alkyl;
R' is $C_1$-$C_5$ alkyl, $C_3$-$C_7$ cycloalkyl or aryl; and
PG is a hydroxy protecting group.

2. The process according to claim 1, wherein
z,25 is a single or double bond;
X is O or NH;
Y is α-OH;
Y' is α-OPG;
Z is $CH_2$ or O;
R is $C_1$-$C_5$ alkyl;
R' is phenyl optionally substituted by $C_1$-$C_5$ haloalkyl or halogen; and
PG is a hydroxy protecting group.

3. The process according to claim 1, wherein
----- is a single or double bond;
X is O or NH;
Y is α-OH;
Y' is α-OPG;
Z is $CH_2$ or O;
R is $C_1$-$C_5$ alkyl;
R' is phenyl optionally substituted by $CF_3$, Cl or F; and
PG is a hydroxy protecting group.

4. The process according to claim 1, wherein
----- is a single or double bond;
X is O or NH;
Y is α-OH;
Y' is α-OPG;
Z is $CH_2$ or O;
R is $C_1$-$C_5$ alkyl;
R' is phenyl optionally substituted by $CF_3$; and
PG is a hydroxy protecting group.

5. The process according to any one of claims 1 to 4, wherein the hydroxy protecting group is tetrahydropyranyl, trimethylsilyl, triethylsilyl or t-butyldimethylsilyl.

6. The process according to claim 5, wherein the hydroxy protecting group is triethylsilyl.

7. The process according to any one of claims 1 to 4, wherein the hydroxy protecting group of the protected PGE compound of formula (5) is removed under an acidic condition in step (i).

8. The process according to claim 7, wherein the acidic condition is provided by the use of pyridinium p-toluensulfonate.

9. The process according to claim 1, wherein the protected PGE compound of formula (5) in which z,25 is a double bond is prepared by converting an alkenyl tin compound of the following formula (3) to its cuprate, and subjecting the cuprate to conjugate addition to a cyclopentenone compound of the following formula (4):

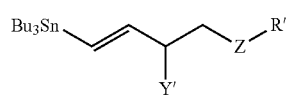

-continued

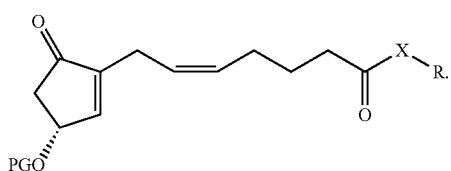

(4)

10. The process according to claim 9, wherein the alkenyl tin compound of formula (3) is added to a solution of $Me_2Cu(CN)Li_2$ and converted to a higher order mixed cuprate of the following formula (7):

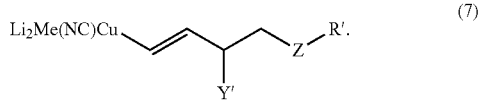

(7)

11. The process according to claim 1, wherein the reduction in step (ii) is carried out by using a reducing agent selected from the group consisting of sodium borohydride ($NaBH_4$), L-selectride, N-selectride, K-selectride, LS-selectride, and 2,6-di-tert-butyl-4-methyl phenol and diisobutyl aluminium hydride (DIBAL).

12. The process according to claim 11, wherein the reducing agent is 2,6-di-tert-butyl-4-methyl phenol and diisobutyl aluminium hydride (DIBAL).

13. The process according to claim 1, wherein the prostaglandin F (PGF) compound of formula (1) in which X is NH is prepared by reacting the PGF derivative of formula (1) in which X is O and R is methyl, with $RNH_2$.

14. The process according to claim 1, which further comprises the step of purifying the prostaglandin F (PGF) compound of formula (1) by HPLC using a mixture of hydrocarbon and alcohol or a mixture of dichloromethane and alcohol.

15. The process according to claim 14, wherein the mixture of hydrocarbon and alcohol is a mixture of n-hexane and anhydrous ethanol or a mixture of n-heptane and anhydrous ethanol.

16. The process according to claim 14, wherein the mixture of dichloromethane and alcohol is a mixture of dichloromethane and isopropanol.

* * * * *